US012324639B2

(12) United States Patent
Tojo et al.

(10) Patent No.: US 12,324,639 B2
(45) Date of Patent: Jun. 10, 2025

(54) SURGICAL SYSTEM AND METHOD OF CONTROLLING SURGICAL MANIPULATOR ARM

(71) Applicant: KAWASAKI JUKOGYO KABUSHIKI KAISHA, Kobe (JP)

(72) Inventors: Tsuyoshi Tojo, Kobe (JP); Nobuyasu Shimomura, Kobe (JP); Tetsuo Ichii, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 510 days.

(21) Appl. No.: 17/782,185

(22) PCT Filed: Dec. 3, 2020

(86) PCT No.: PCT/JP2020/045098
§ 371 (c)(1),
(2) Date: Jun. 3, 2022

(87) PCT Pub. No.: WO2021/112193
PCT Pub. Date: Jun. 10, 2021

(65) Prior Publication Data
US 2023/0000572 A1 Jan. 5, 2023

(30) Foreign Application Priority Data
Dec. 5, 2019 (JP) ................. 2019-220284

(51) Int. Cl.
A61B 34/30 (2016.01)
A61B 34/00 (2016.01)
A61B 90/00 (2016.01)

(52) U.S. Cl.
CPC .............. *A61B 34/30* (2016.02); *A61B 34/00* (2016.02); *A61B 90/361* (2016.02)

(58) Field of Classification Search
CPC ....... A61B 34/30; A61B 34/00; A61B 90/361; A61B 34/37
See application file for complete search history.

(56) References Cited

U.S. PATENT DOCUMENTS

| 5,737,500 A | 4/1998 | Seraji et al. | |
| 9,291,793 B2* | 3/2016 | Cooper | G02B 7/001 |
| 11,253,336 B2* | 2/2022 | Yi | A61B 34/30 |
| 11,259,886 B2* | 3/2022 | Weir | A61B 34/37 |
| 2006/0167440 A1* | 7/2006 | Cooper | A61B 34/71 |
| | | | 606/1 |

(Continued)

FOREIGN PATENT DOCUMENTS

JP   2017-104452 A   6/2017

*Primary Examiner* — Sohana Tanju Khayer
(74) *Attorney, Agent, or Firm* — METROLEX IP LAW GROUP, PLLC; Robert L. Scott, Esq.

(57) ABSTRACT

A controller of a surgical system is configured to: set a center point; set a reference point on a reference line that is an extension of a rotation axis of a proximal end roll joint or that is offset from the extension in a direction normal to the extension; and position joints of a manipulator arm such that a shaft passes through the center point and that a reference plane passes through the reference point, the reference plane including a rotation axis of a distal end roll joint that coincides with a central axis of the shaft and crossing a rotation axis of a pivotal joint.

21 Claims, 9 Drawing Sheets

(56) References Cited

U.S. PATENT DOCUMENTS

| | | | | |
|---|---|---|---|---|
| 2011/0245844 | A1* | 10/2011 | Jinno | A61B 34/30 |
| | | | | 606/130 |
| 2013/0024024 | A1* | 1/2013 | Namiki | A61B 1/00149 |
| | | | | 700/245 |
| 2013/0325030 | A1* | 12/2013 | Hourtash | B25J 9/1676 |
| | | | | 606/130 |
| 2017/0066131 | A1* | 3/2017 | Kamikawa | B25J 9/1697 |
| 2017/0172670 | A1* | 6/2017 | Swarup | A61B 34/30 |
| 2017/0273748 | A1* | 9/2017 | Hourtash | B25J 9/1607 |
| 2018/0036089 | A1* | 2/2018 | Nakanishi | B25J 15/00 |
| 2018/0289445 | A1* | 10/2018 | Krinninger | A61B 34/70 |
| 2018/0360550 | A1 | 12/2018 | Nakanishi | |
| 2019/0083186 | A1 | 3/2019 | Zietlow et al. | |
| 2019/0298465 | A1* | 10/2019 | Chin | A61B 17/3201 |
| 2020/0038116 | A1* | 2/2020 | Toporek | A61B 34/20 |
| 2021/0030496 | A1* | 2/2021 | Devengenzo | A61B 34/30 |
| 2021/0161606 | A1* | 6/2021 | Hares | A61B 34/37 |
| 2022/0008147 | A1* | 1/2022 | Crawford | A61B 34/30 |
| 2023/0000572 | A1* | 1/2023 | Tojo | A61B 34/37 |
| 2023/0112200 | A1* | 4/2023 | Steger | A61B 90/50 |
| | | | | 606/130 |

\* cited by examiner

SURGICAL SYSTEM AND METHOD OF CONTROLLING SURGICAL MANIPULATOR ARM

CROSS-REFERENCE TO RELATED APPLICATIONS

This application is a national stage entry of International Application No. PCT/JP2020/045098 filed on Dec. 3, 2020, which claims priority based on the Article 8 of Patent Cooperation Treaty from the prior Japanese Patent Application No 2019-220284, filed on Dec. 5, 2019, the entire contents of all of which are incorporated herein by reference.

TECHNICAL FIELD

The present invention relates to a surgical system and a method of controlling a surgical manipulator arm.

BACKGROUND ART

A surgical system that performs surgery by moving manipulator arms has been conventionally known (see Patent Literature 1, for example).

In this surgical system, the proximal ends of the manipulator arms are removably mounted on a platform, and the manipulator arms are arranged adjacent to one another.

CITATION LIST

Patent Literature

PTL 1: Japanese Laid-Open Patent Application Publication No. 2017-104452

SUMMARY OF INVENTION

Technical Problem

However, the surgical system described in Patent Literature 1 is disadvantageous in that when any of the manipulator arms is moved, the manipulator arm is likely to interfere with another component, such as the adjacent manipulator arm, of the surgical system or with the surrounding environment.

Solution to Problem

In order to solve the above problem, a surgical system according to one aspect includes: a surgical tool including a shaft and a distal end roll joint having a rotation axis coinciding with a central axis of the shaft; a manipulator arm holding the surgical tool at a distal end thereof and having seven or more degrees of freedom, the manipulator arm including joints and actuators that drive the joints to effect positioning of the joints, the joints including a proximal end roll joint disposed at a proximal end of the manipulator arm, and a pivotal joint disposed between the proximal end roll joint and the distal end roll joint, the pivotal joint having a rotation axis crossing a reference plane including the rotation axis of the distal end roll joint, the rotation axis of the pivotal joint being in a fixed orientation relative to the reference plane; a console that receives an operation input provided by an operator to the manipulator arm; and a controller that controls the actuators based on the operation input, wherein the controller is configured to: set a center point; set a reference point on a reference line that is an extension of a rotation axis of the proximal end roll joint or that is offset from the extension in a direction normal to the extension; and position the joints such that the shaft passes through the center point and that the reference plane passes through the reference point.

In this configuration, the motion of the manipulator arm can be controlled such that most of the rotational motion of the shaft can be effected by the motion of the distal end roll joint, and the manipulator arm can be prevented from significantly changing its posture to effect the rotational motion of the shaft. As such, interference of the manipulator arm with another component of the surgical system or with the surrounding environment can be prevented.

Advantageous Effects of Invention

The present invention has the advantage of preventing interference of a manipulator arm of a surgical system with another component of the surgical system or with the surrounding environment.

DESCRIPTION OF EMBODIMENTS

Hereinafter, exemplary embodiments will be described with reference to the drawings. The present invention is not limited by the embodiments described below. In the following, the same or like elements are denoted by the same reference signs throughout the drawings and will not be described repeatedly.

Embodiment 1

Figure 1:
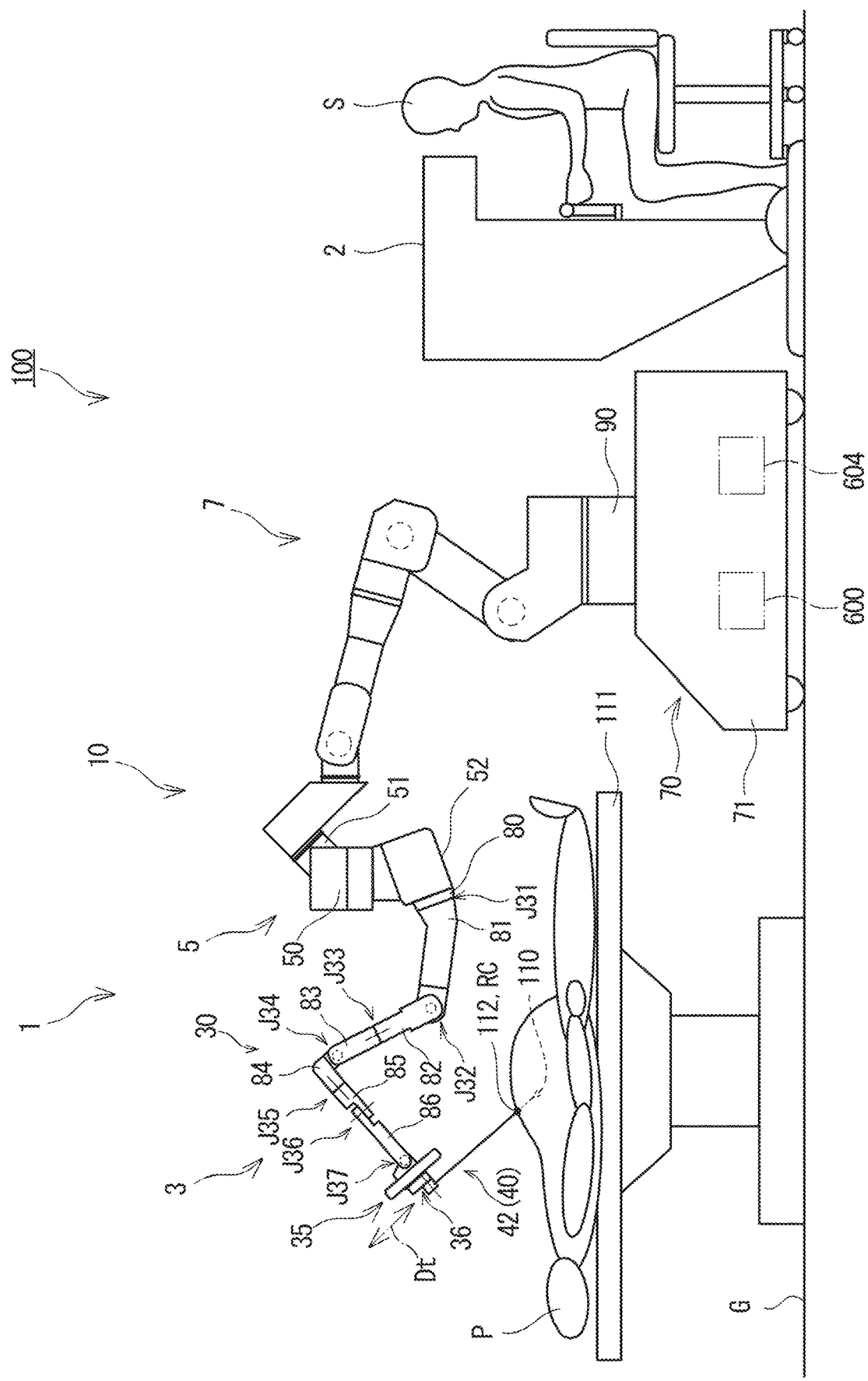
FIG. 1 is a front view showing an example of the configuration of a surgical system according to Embodiment 1.
Figure 2:
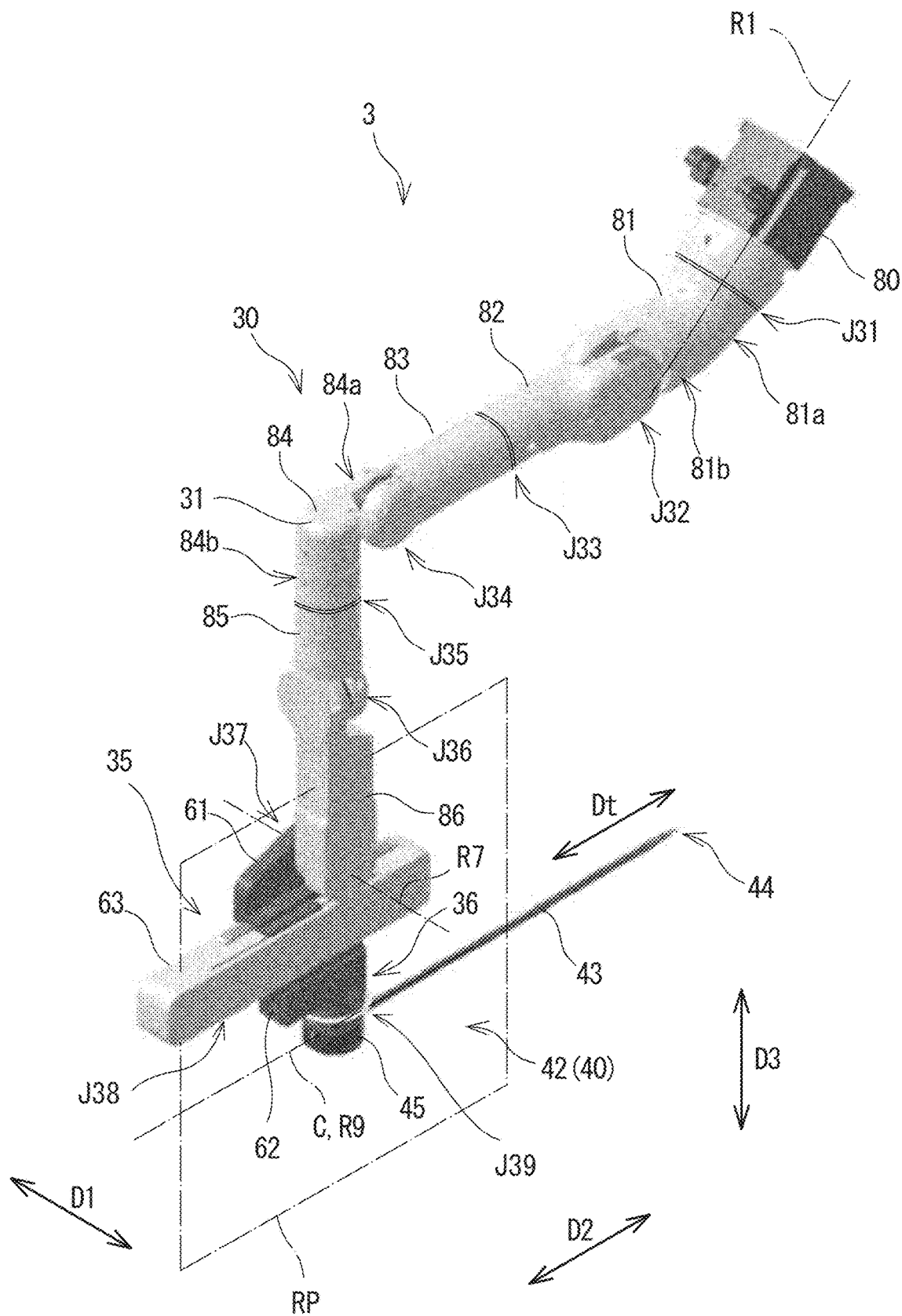
FIG. 2 is a perspective view showing an example of the overall configuration of a manipulator arm of the surgical system of FIG. 1.
Figure 3:
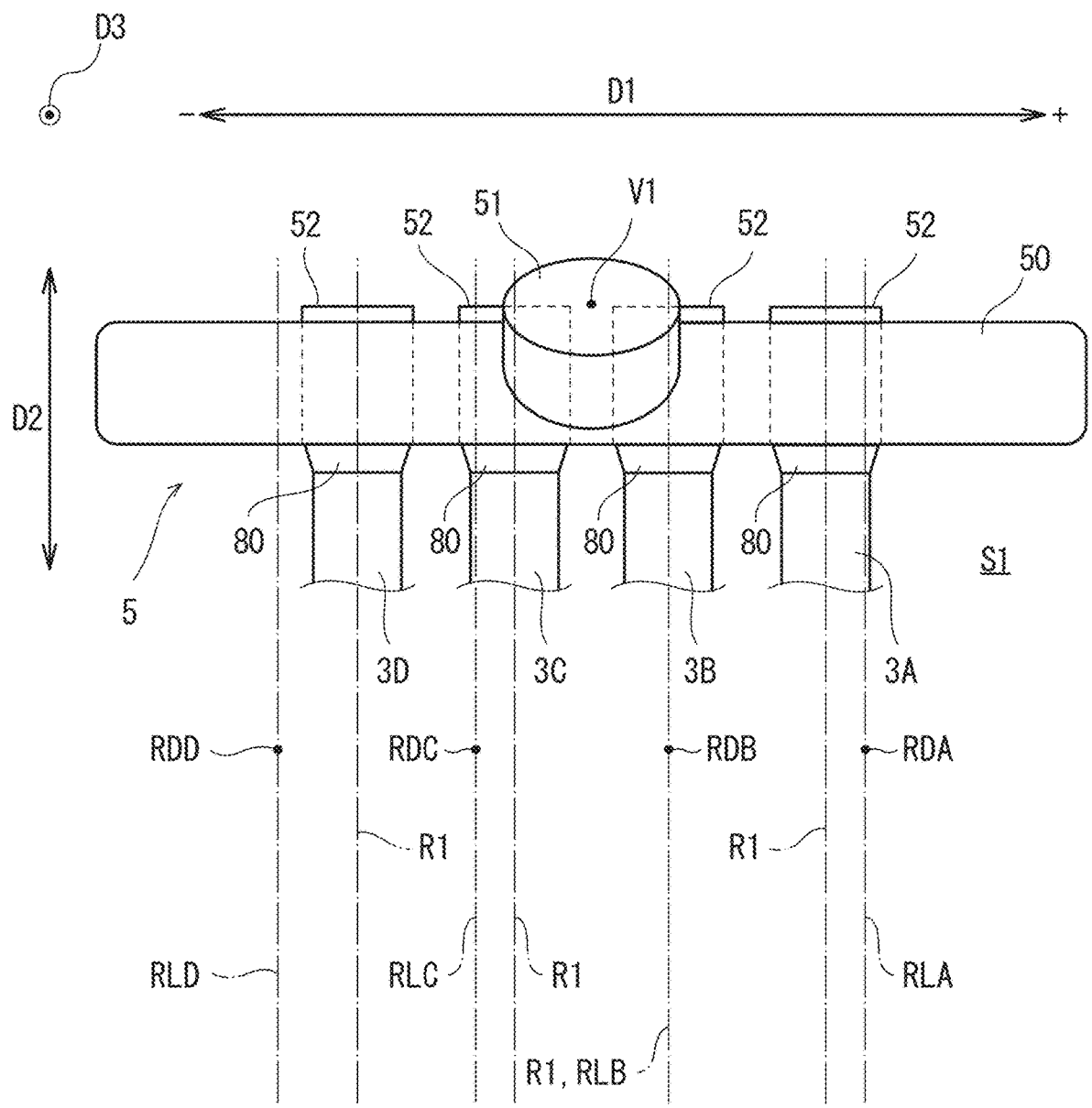
FIG. 3 is a plan view showing an example of the configuration of an arm base of the surgical system of FIG. 1.

FIG. 1 is a schematic view showing the overall configuration of a surgical system 100 according to Embodiment 1. FIG. 2 is a schematic view showing the overall configuration of a manipulator arm 3 of the surgical system 100 shown in FIG. 1. FIG. 3 is a plan view showing an example of the configuration of an arm base 5. The surgical system 100 is configured for procedures such as robot-assisted surgery and robotic remote surgery, in which an operator S such as a surgeon performs endoscopic surgery on a patient P using a patient-side system 1. FIG. 1 shows a state where a positioner 7, the arm base 5, and the manipulator arms 3 have been placed in given preparatory positions (which will be described in detail later) before surgery. The size ratio between the positioner 7 and manipulator arms 3 depicted in FIG. 1 is different from the real size ratio. The size ratio of the manipulator arms 3 to the positioner 7 is smaller in reality than in the configuration of FIG. 1.

The surgical system 100 includes the patient-side system 1 and a console 2 (see FIG. 4 described later) used to operate the patient-side system 1. The console 2 is placed away from the patient-side system 1, and the patient-side system 1 is remotely operated using the console 2 during surgery. The operator S provides to the console 2 inputs representing the operation to be performed by the patient-side system 1 and including an operation input for the manipulator arm 3, and the console 2 transmits the corresponding operation command to the patient-side system 1. The patient-side system 1 receives the operation command transmitted from the console 2 and, based on the operation command, moves an end effector 44 mounted on the patient-side system 1.

The console 2 serves as an interface between the surgical system 100 and the operator S and is used to operate the patient-side system 1. The console 2 is placed in a surgery room and near or far from a surgical bed 111 or placed outside the surgery room. The console 2 includes: operation inputters such as a manually-operated manipulator arm and a foot-operated pedal which are used by the operator S to input operation commands; and a monitor that displays an image captured by an endoscope assembly attached as a surgical tool 40 to the patient-side system 1. The operator S maneuvers the operation inputters to input an operation command to the console 2 while viewing an affected zone (surgical site 110) on the monitor. The operation command input to the console 2 is transmitted to a controller 600 (the details of which will be described later) of the patient-side system 1 by wire or wirelessly.

The patient-side system 1 serves as an interface between the surgical system 100 and the patient P. The patient-side system 1 is placed in the surgery room and near the surgical bed 111 on which the patient P lies. The vicinity of the surgical bed 111 in the surgery room is a sterile field subjected to sterilization.

The patient-side system 1 includes the positioner 7, the arm base (platform) 5 mounted on the distal end of the positioner 7, patient-side manipulator arms (simply referred to as "arms 3" hereinafter) removably mounted on the arm base 5, a shaft 43, and the end effector 44. The positioner 7 extends from a given support and connects the support and the arm base 5. In the present embodiment, the positioner 7 is configured as a vertical articulated robot, in particular a multi-articulated (seven axis-articulated) arm having multiple degrees of freedom (seven degrees of freedom). The positioner 7 can move the arm base 5 three-dimensionally (in X-axis, Y-axis, and Z-axis directions orthogonal to one another) relative to a movable cart 70 serving as the given support. The positioner 7, the arm base 5, and components of each arm 3 which are arranged in order from the proximal end of the arm 3 to a holder 36 of the arm 3, are covered by a non-illustrated sterile drape, and thus the positioner 7, the arm base 5, and the components of each arm 3 which are arranged in order from the proximal end to the holder 36 described later, are separated from the sterile field in the surgery room.

Each of the arms 3 includes a tool holder (holder 36) capable of holding the surgical tool 40 including an elongated shaft. The endoscope assembly is held by the holder 36 of one of the arms 3. Instruments 42 are removably held by the holders 36 of the other arms 3. Hereinafter, the arm 3 equipped with the endoscope assembly may be referred to as a "camera arm", and each arm 3 equipped with the instrument 42 may be referred to as an "instrument arm". As shown in FIG. 3, the patient-side system 1 of the present embodiment includes four arms 3A, 3B, 3C, and 3D, one of which is a camera arm and the other three of which are instrument arms. In explanation of a feature specific to a particular one of the arms 3A, 3B, 3C, and 3D, the arm of interest is clearly indicated by adding the letter "A", "B", "C", or "D" after the numeral 3. In explanation of a feature common to the four arms 3A, 3B, 3C, and 3D, the letters "A", "B", "C", and "D" are not added after the numeral 3. The same applies to reference lines RL and reference points RD described later.

Each arm 3 is a mechanism that performs the function of changing the position and posture of the shaft 43. The surgical tool 40 is removable from the holder 36 as previously stated, and a tool base 45 and a ninth joint J39 described later are defined as elements included in the surgical tool 40. The tool base 45 and ninth joint J39 may be elements included in the arm 3.

In the patient-side system 1, the arm base 5 functions as a "hub" for the arms 3. In the present embodiment, the positioner 7 and the arm base 5 constitute a manipulator arm support 10 movably supporting the arms 3. The positioner 7 need not be a vertical articulated robot. For example, the positioner 7 may be a linear motion rail for supporting the arm base 5, a lifting machine, or a bracket mounted on a ceiling or wall. The given support to which the positioner 7 is connected is not limited to a movable support such as the cart 70. For example, the given support may be a wall or floor of the surgery room or an object fixed to the wall or floor.

The elements of the patient-side system 1 are serially connected in order from the positioner 7 to the endoscope assembly or each instrument 42. For the serially connected elements, their ends directed towards the positioner 7 (in particular, a base 90 at which the positioner 7 is connected to the cart 70) may be herein referred to as "proximal ends", and the opposite ends may be herein referred to as "distal ends". The term "base end" is interchangeable with "proximal end", and the term "leading end" is interchangeable with "distal end".

The operation of the patient-side system 1 is controlled by the controller 600. The controller 600 is configured, for example, by a computer such as a microcontroller and includes a processor (processing circuitry) such as a CPU. The controller 600 may consist of a single controller that performs centralized control or may be constituted by controllers that cooperate to perform distributed control. Memories such as a ROM and a RAM are disposed in the interior of a cart body 71. The controller 600 and a storage 602 storing control programs and various data used for operation control are also installed in the interior of the cart body 71. The cart body 71 is equipped with an operation interface 604 used mainly to set and input the positions and postures (preparatory postures described later) to be assumed by the positioner 7, arm base 5, and arms 3 before surgery. The operation interface 604 is configured, for example, by a touch panel.

Hereinafter, the arm base 5 and manipulator arms 3 will be described in detail.

As shown in FIG. 3, the arm base 5 includes an arm base body 50, a positioner mount 51 which is disposed at the top (proximal end) of the arm base body 50 and on which the distal end of the positioner 7 is mounted, and at least one arm mount 52 which is disposed at the bottom of the arm base body 50 and on which the proximal ends of the arms 3 are mounted. The arm base 5 is configured to be rotatable relative to the distal end of the positioner 7. In the present embodiment, the arm base 5 includes the arm mounts 52 (the number of which is four) disposed in one-to-one correspondence with the arms 3 (the number of which is four). The arm base 5 has an elongated shape. The bases 80 of the arms 3 are secured to the arm mounts 52, and thus the proximal end (first link 81 described later) of each arm 3 is configured to be rotatable about a rotation axis of a first joint J31 described later.

Specifically, the proximal ends (bases 80) of the arms 3 are mounted on the arm mounts 52 so as to be arranged in a single row in a given first direction D1. The first direction D1 is a direction defined (included) in a given first plane S1. In the present embodiment, the first plane S1 is an imaginary plane that is parallel to a floor surface (horizontal plane) G when the arm base 5 is in a preparatory position (FIG. 1), and the first direction D1 is, for example, a horizontal direction coinciding with the longitudinal direction of the elongated arm base 5. However, the first plane S1 and the first direction D1 are not limited to those in the present embodiment. The first direction D1 is a direction normal to the rotation axis R1 of the later-described first joint J31 of each arm 3. That is, the arm mounts 52, as viewed from above when the arm base 5 is in the preparatory position, are arranged in a single row in the first direction D1 (the direction orthogonal to the plane of FIG. 1) and oriented in a second direction D2 orthogonal to the first direction D1. The arm mounts 52 are not limited to being arranged in a single row, and may be arranged in two rows. Alternatively, one or some of the arm mounts 52 may be offset relative to the other arm mounts 52 in the second direction D2. Alternatively, one or some of the arm mounts 52 may be offset relative to the other arm mounts 52 in a third direction D3. The third direction D3 is, for example, a vertical direction (the direction orthogonal to the plane of FIG. 3).

FIG. 2 shows a schematic configuration of one of the arms 3 of the patient-side system 1, the one arm 3 being equipped with the instrument 42. In the present embodiment, the arms 3 of the patient-side system 1 have the same or similar configurations. Alternatively, at least one of the arms 3 may have a different configuration (such as having different degrees of freedom) than the other arms 3. As shown in FIG. 2, the arm 3 includes an arm body 30, a translational motion unit 35 coupled to the distal end of the arm body 30, the holder (tool holder) 36 disposed at the distal end of the translational motion unit 35 and capable of holding the surgical tool 40 in the shape of an elongated shaft, and the tool base 45 of the instrument 42. The arm bodies 30 are configured such that their distal ends are movable three-dimensionally relative to their proximal ends.

The arms 3 are configured to be removable from the arm base 5.

The arm body 30 includes the base 80 removably mounted on the arm base 5 and arm links serially coupled in order from the base 80 to the distal end of the arm body 30. The arm body 30 includes joints via which the arm links are serially coupled such that each of the arm links is rotatable relative to another of the arm links. The arm links include first to sixth links 81 to 86. The joints include first to seventh joints J31 to J37. The joints in the present embodiment are configured as rotary joints having rotation axes. Alternatively, at least one of the joints may be configured as a prismatic joint.

Specifically, the proximal end of the first link 81 is coupled to the distal end of the base 80 via the first joint J31 which is a torsional (roll) joint (proximal end roll joint). The proximal end of the second link 82 is coupled to the distal end of the first link 81 via the second joint J32 which is a bending (pitch) joint. The proximal end of the third link 83 is coupled to the distal end of the second link 82 via the third joint J33 which is a torsional joint. The proximal end of the fourth link 84 is coupled to the distal end of the third link 83 via the fourth joint J34 which is a pivotal joint. The proximal end of the fifth link 85 is coupled to the distal end of the fourth link 84 via the fifth joint J35 which is a torsional joint. The proximal end of the sixth link 86 is coupled to the distal end of the fifth link 85 via the sixth joint J36 which is a pivotal joint. The proximal end of the translational motion unit 35 is coupled to the distal end of the sixth link 86 via the joint J37 which is a pivotal joint (distal end-side pivotal joint).

In the present embodiment, the first link 81 is shaped to be bent between the adjacent joints J31 and J32. In other words, the first link 81 is configured such that the rotation axes of the first and second joints J31 and J32 do not cross each other. That is, the first link 81 includes a first portion 81a and a second portion 81b. The first portion 81a extends from the proximal end-side first joint J31 in a given first direction (the direction of the rotation axis of the first joint J31). The second portion 81b extends from the distal end of the first portion 81a in a second direction crossing the direction in which the first portion 81a extends (and orthogonal to the rotation axis of the second joint J32), and is connected to the distal end-side second joint J32. The angle between the first and second directions in the first link 81 is, for example, from 120 to 160 degrees (e.g., 140 degrees). The first and second portions 81a and 81b are smoothly continuous with each other. Thus, a wire such as that for electrical connection can be easily inserted through the arm links despite the bent shape of one of the arm links.

Additionally, the fourth link 84 is shaped to be bent between the adjacent joints J34 and J35, and this bent portion is an elbow 31 of the arm body 30. In other words, the fourth link 84 is configured such that the rotation axes of the fourth and fifth joints J34 and J35 do not cross each other. The rotation axis of the fifth joint J35 is offset relative to the rotation axis of the fourth joint J34 in a direction orthogonal to the rotation axes of the fourth and fifth joints J34 and J35. That is, the fourth link 84 includes a first portion 84a and a second portion 84b. The first portion 84a extends from the proximal end-side fourth joint J34 in a given first direction (the direction orthogonal to both of the rotation axes of the fourth and fifth joints J34 and J35). The second portion 84b extends from the distal end of the first portion 84a in a second direction (the direction of the rotation axis of the fifth joint J35) crossing the direction in which the first portion 84a extends, and is connected to the distal end-side fifth joint J35. The angle between the first and second directions in the fourth link 84 is, for example, from 70 to 110 degrees (e.g., 90 degrees). The first and second portions 84a and 84b are smoothly continuous with each other.

Each of the other links 82, 83, 85, and 86 is shaped to extend straight between the adjacent joints. In other words, each of the other links 82, 83, 85, and 86 is configured such that the rotation axes of the adjacent joints cross each other.

Each of the arm links is configured such that the area of the transverse cross-section of the arm link is smaller than that of another arm link (or the base 80) connected to the proximal end of the arm link. Thus, the arm body 30 is configured to gradually become thinner from its proximal end towards its distal end. Each of the joints J32, J34, and J36, which are pivotal joints, is configured such that the distal end of the arm link 81, 83, or 85 connected to the proximal end of the joint J32, J34, or J36 is located on one side with respect to the center of the joint J32, J34, or J36 in the direction of the rotation axis of the joint J32, J34, or J36. Additionally, each of the joints J32, J34, and J36 is configured such that the proximal end of the arm link 82, 84, or 86 connected to the distal end of the joint J32, J34, or J36 is located on the other side with respect to the center of the joint J32, J34, or J36 in the direction of the rotation axis of the joint J32, J34, or J36 and opposed to the distal end of the arm link 81, 83, or 85 connected to the proximal end of the joint J32, J34, or J36.

Furthermore, the width of each of the joints J32, J34, and J36, i.e., the distance in the direction of the rotation axis of the J32, J34, or J36 between the outermost point on the distal end of the arm link 81, 83, or 85 connected to the proximal end of the J32, J34, or J36 and the outermost point on the proximal end of the arm link 82, 84, or 86 connected to the distal end of the J32, J34, or J36, is smaller than the diameter (maximum dimension) of the transverse cross-section of a portion of the arm link 81, 83, or 85 that is closer to the proximal end of the arm link 81, 83, or 85 than the distal end of the arm link 81, 83, or 85.

As described above, each joint and the arm link connected to the distal end of the joint are configured to have a smaller width than the arm link connected to the proximal end of the joint. Thus, the movement range of each arm body 30 (the range over which the arm body 30 does not interfere with any other arm body 30) can be extended in the workspace which narrows towards the surgical site 110 of the patient P.

The outer shell of the arm body 30 is made of a material having chemical resistance imparted by coating. An opening such as an access hole of the arm body 30 is covered with a cover made of resin. Making the cover with a material such as resin can reduce the weight of a portion of the arm body 30 that is not responsible for the strength of the arm body 30. Thus, in the event that the cover is dropped or the arm body 30 collides with another arm body 30, a surgery assistant, or any other object, the resulting impact can be mitigated. The outer shell itself of the arm body 30 may include a portion made of a resin material.

The translational motion unit 35 is a mechanism by which the holder 36 attached to the distal end of the translational motion unit 35 is moved in translation along a long axis direction Dt described later to move the instrument 42 attached to the holder 36 in translation along a direction in which the shaft 43 described later extends.

The translational motion unit 35 includes: a proximal end-side link 61 coupled to the distal end of the sixth link 86 of the arm body 30 via the seventh joint J37 which is a pivotal joint; a distal end-side link 62; a coupling link 63 that is disposed between, and moves in conjunction with, the proximal end-side link 61 and the distal end-side link 62; and an interlocking mechanism. The seventh joint J37 extends in a direction orthogonal to the long axis direction Dt. A drive source of the translational motion unit 35 is disposed at the proximal end-side link 61. The coupling link 63 extends in the long axis direction Dt.

In the translational motion unit 35, the relative position between the proximal end-side link 61 and coupling link 63 in the long axis direction Dt is changeable. In the translational motion unit 35, upon a change in the relative position between the proximal end-side link 61 and coupling link 63, the relative position between the coupling link 63 and distal end-side link 62 in the long axis direction Dt is also changed by the action of the interlocking mechanism. Thus, the translational motion unit 35 can change the position of the instrument 42, which is attached to the holder 36 mounted on the distal end-side link 62, relative to the proximal end-side link 61 in the long axis direction Dt. The translational motion unit 35 can advance the instrument 42 in an insertion direction or withdraw the instrument 42 in a removal direction. More specifically, the coupling link 63 includes a pair of guide rails extending in the long axis direction Dt. One of the guide rails supports the proximal end-side link 61 such that the proximal end-side link 61 is slidable in the long axis direction Dt, while the other guide rail supports the distal end-side link 62 such that the distal end-side link 62 is slidable in the long axis direction Dt. Once the proximal end-side link 61 slides on the one of the guide rails to one side in the long axis direction Dt, the interlocking mechanism causes the distal end-side link 62 to slide on the other guide rail to the opposite side in the long axis direction Dt. The interlocking mechanism is a double-speed mechanism and may be, for example, a mechanism employing a pulley and a timing belt or a mechanism including a gear train. The translational motion unit 35 serves as an eighth joint J38 which is a prismatic joint that couples the distal end-side link 62 and holder 36 to the proximal end-side link 61 and that moves the distal end-side link 62 and holder 36 linearly in the long axis direction Dt.

The holder 36 removably holds the tool base 45 of the surgical tool 40 described later. The holder 36 includes a drive shaft that is rotationally driven, and generates drive power for rotating the shaft 43 described later.

The instrument 42 includes: the tool base 45 disposed at the proximal end of the instrument 42; the shaft 43 having a proximal end connected to the tool base 45; and the end effector (treatment tool) 44 connected to the distal end of the shaft 43. The instrument 42 further includes a drive power transmitter that is connected to the drive shaft of the holder 36 by attaching the instrument 42 to the holder 36 and through which the drive power of the drive shaft is transmitted. The long axis direction Dt is defined for the instrument 42, and the tool base 45, shaft 43, and end effector 44 are arranged in this order in the long axis direction Dt. The end effector 44 of the instrument 42 is selected from the group including tools having movable joints (such as forceps, scissors, graspers, needle holders, microdissectors, staple appliers, tackers, suction and irrigation tools, snare wires, and clip appliers) and tools having no joints (such as cutting blades, cautery probes, irrigators, catheters, and suction orifices). The proximal end of the shaft 43 is coupled to the tool base 45 via the ninth joint J39 which is a torsional (roll) joint (distal end roll joint). The ninth joint J39 has a rotation axis R9 coinciding with the central axis C of the shaft 43. The rotation axis of a joint herein refers to a geometric (imaginary) axis of a rotating shaft. In the present embodiment, as previously stated, the tool base 45 and ninth joint J39 may be elements included in the arm 3 to effect positioning of the shaft 43.

As previously stated, the eighth joint J38 located between the seventh and ninth joints J37 and J39 is a prismatic joint. Thus, the orientation of the rotation axis R9 of the ninth joint J39 is fixed relative to the rotation axis R7 of the seventh joint J37. The rotation axis R7 of the seventh joint J37 is orthogonal to a reference plane RP including that rotation axis R9 of the ninth joint J39 which extends in the long axis direction Dt. That is, in the present embodiment, the seventh joint J37 serves as a pivotal joint defining the reference plane RP. The angle between the rotation axis R7 and the reference plane RP is not limited to the right angle, and the rotation axis R7 and the reference plane RP may cross each other at any angle. Rotating the seventh joint J37 can result in the shaft 43 pivoting upward or downward.

In the case where the arm 3 is an instrument arm, the instrument 42 is removably held by the holder 36. The shaft 43 of the instrument 42 held by the holder 36 extends in the long axis direction Dt. In the case where the arm 3 is a camera arm, the endoscope assembly having a camera mounted at the distal end of the shaft 43 is removably held by the holder 36. The holder 36 of the camera arm has the same shape and structure as the holder 36 of the instrument arm, but may have a different shape or structure than the holder 36 of the instrument arm.

Figure 4:
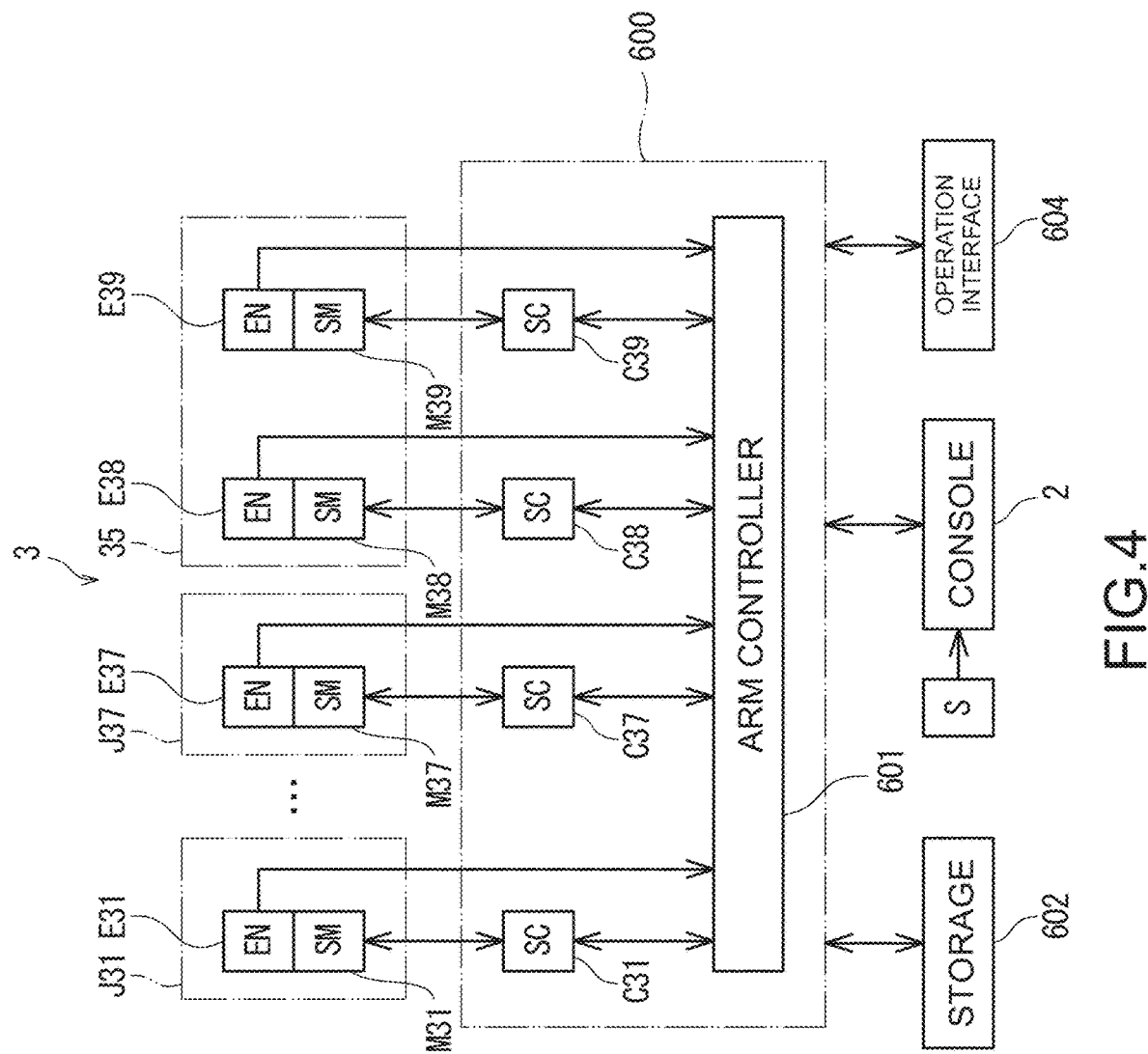
FIG. 4 is a block diagram schematically showing an example of the control system configuration of the surgical system of FIG. 1.

FIG. 4 is a block diagram schematically showing an example of the control system configuration of the surgical system 100 shown in FIG. 1. The arm body 30 configured as described above is equipped with drive servo motors M31 to M37 (denoted by "SM" in FIG. 4) associated respectively with the joints J31 to J37 of the arm body 30, encoders E31 to E37 (denoted by "EN" in FIG. 4) that respectively detect the rotation angles of the servo motors M31 to M37, and reduction gears (not shown) that respectively reduce the speeds output from the servo motors M31 to M37 and increase the torques output from the servo motors M31 to M37.

In FIG. 4, the first and seventh joints J31 and J37 are shown as representatives among the joints J31 to J37 of the arm body 30, and control systems for the other joints J32 to J36 are omitted. The translational motion unit 35 is equipped with a servo motor M38 for translational motion of the eighth joint J38 (servo motor that drives the interlocking mechanism), a servo motor M39 for rotational motion of the ninth joint J39, encoders E38 and E39 that respectively detect the rotation angles of the servo motors M38 and M39, and reduction gears (not shown) that respectively reduce the speeds output from the servo motors M38 and M39 and increase the torques output from the servo motors M38 and M39.

The encoders E31 to E39 are examples of rotational position detectors that detect the rotational positions (rotation angles) of the servo motors M31 to M39, and other rotational position detectors such as resolvers may be used instead of the encoders E31 to E39.

The controller 600 includes an arm controller 601 that controls the movement of the arms 3 based on operation commands. Servo controllers C31 to C39 are electrically connected to the arm controller 601, and actuators associated with the servo motors M31 to M39 are also electrically connected to the arm controller 601 via, for example, amplification circuits.

In the above configuration, a position and posture command indicating a position and posture of the distal end of the arm 3 is input to the arm controller 601 based on an operation command input to the console 2 during surgery. The arm controller 601 generates and outputs position command values based on the position and posture command and the rotation angles detected by the encoders E31 to E39. The servo controllers C31 to C39 having acquired the position command values generate and output drive command values (torque command values) based on the rotation angles detected by the encoders E31 to E39 and the position command values. The amplification circuits having acquired the drive command values supply drive currents matching the drive command values to the servo motors M31 to M39. In this manner, the servo motors M31 to M39 are servo-controlled such that the distal end of the arm 3 is placed in the position and posture matching the position and posture command.

The controller 600 includes the storage 602 from which the arm controller 601 can retrieve data, and the storage 602 prestores surgical information input through the console 2. The surgical information includes a combination of the arms 3 used for surgery.

Additionally, the storage 602 stores information such as the length in long axis direction Dt of the surgical tool 40 (endoscope assembly or instrument) held at the distal end of the arm 3. Thus, the arm controller 601 can identify the position of the distal end of the surgical tool 40 held at the distal end of the arm 3 based on the position and posture command indicating the position and posture of the distal end of the arm 3.

The storage 602 further prestores given preparatory positions (e.g., the positions and postures of the elements 7, 5, and 3 as shown in FIG. 1) in which the arm base 5 and the arms 3 are placed before surgery. The storage 602 may store different preparatory positions depending on factors such as the contents (type) of the surgery and the surgical site.

<Example of Operation of Surgical System>

Figure 5:
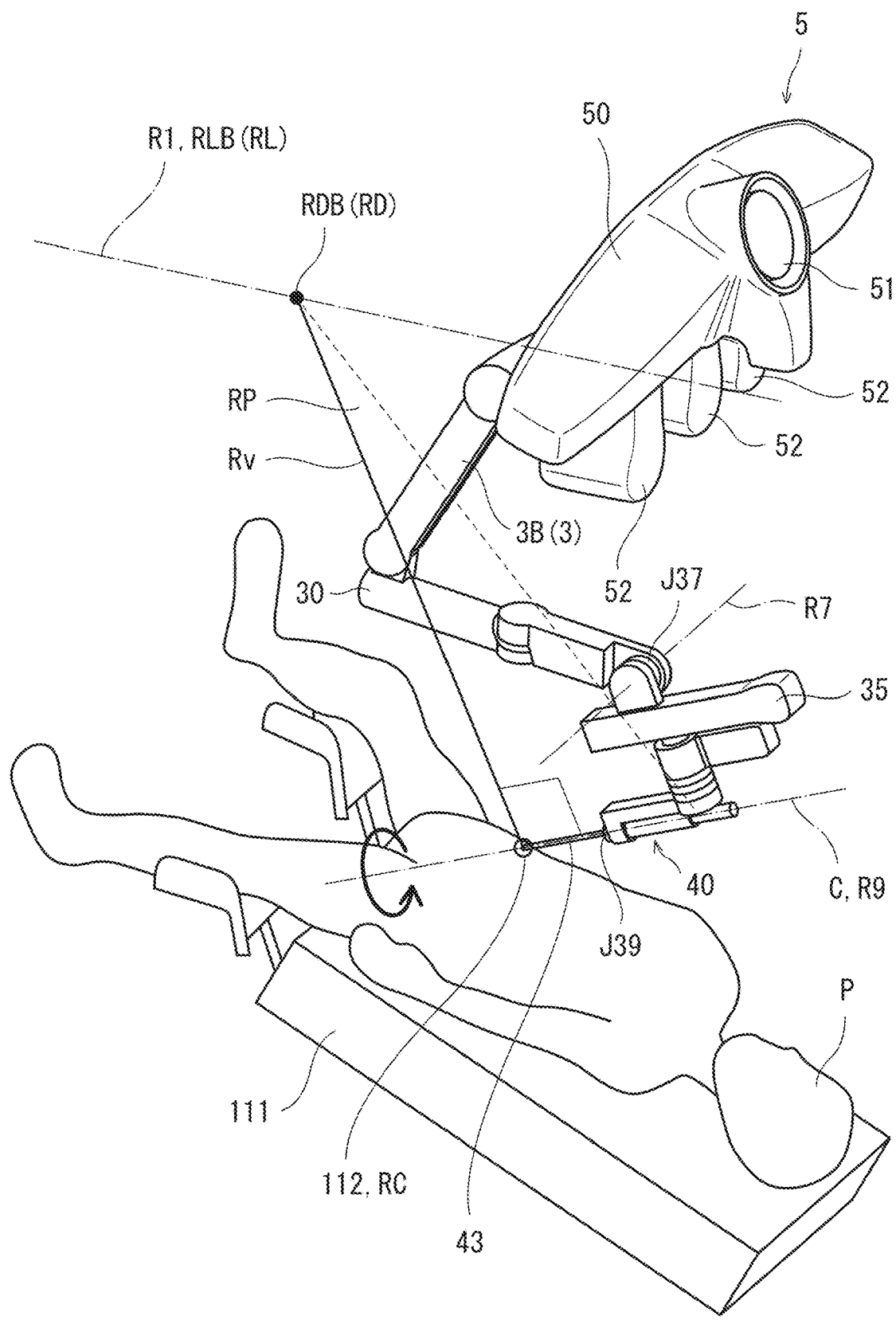
FIG. 5 shows an example of the operation of the surgical system of FIG. 1.
Figure 6:
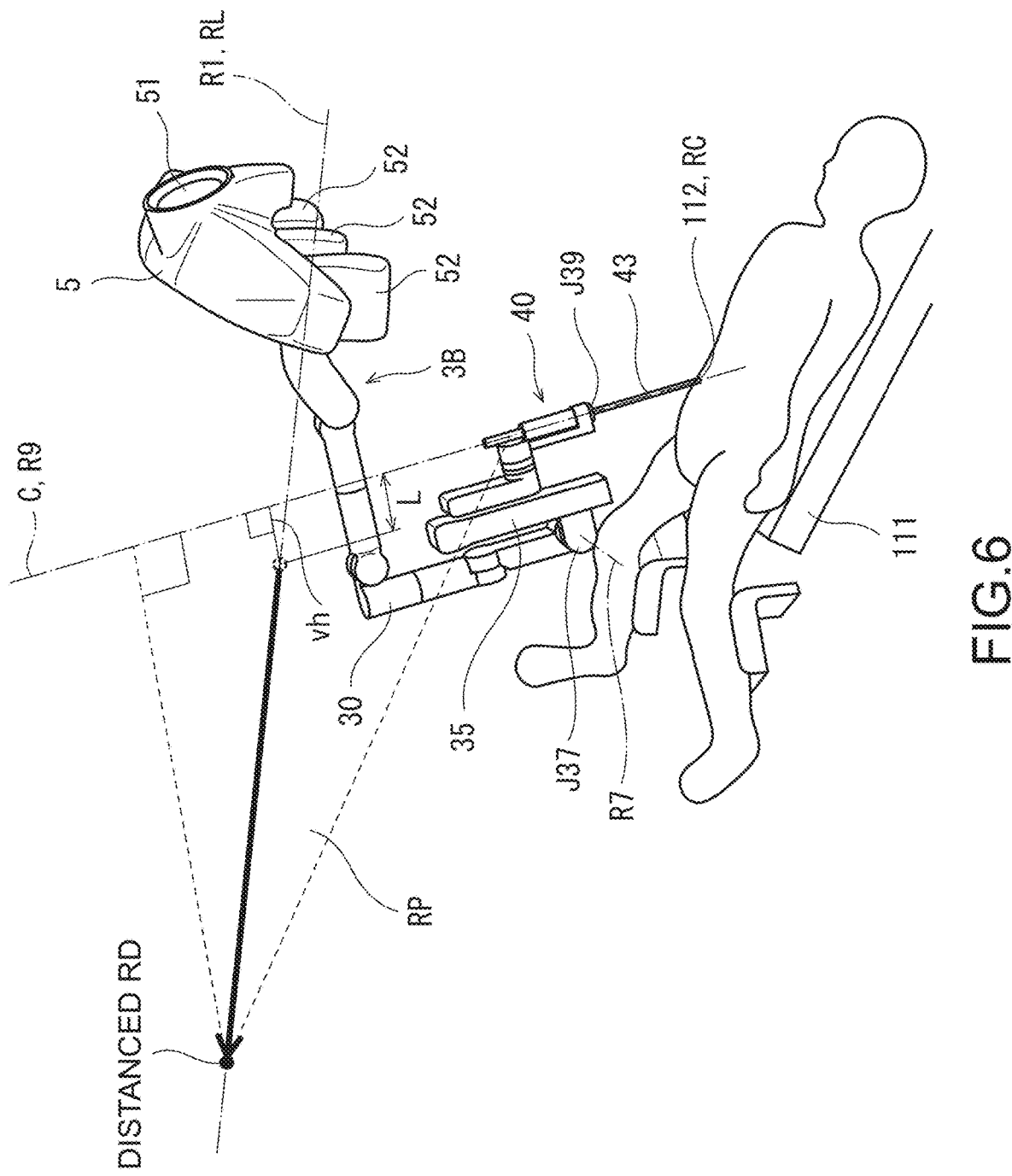
FIG. 6 shows an example of the operation of the surgical system of FIG. 1.
Figure 7:
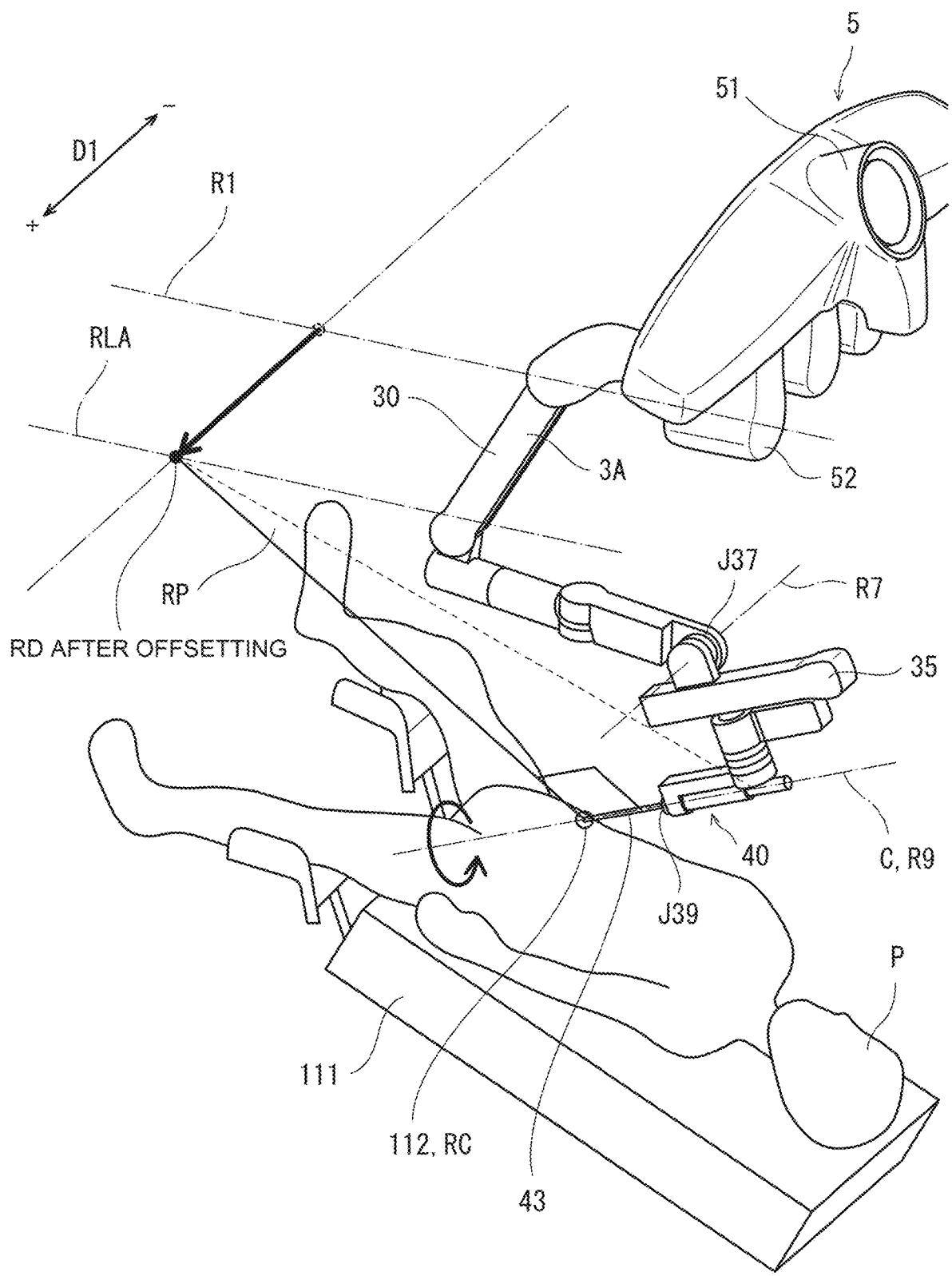
FIG. 7 shows an example of the operation of the surgical system of FIG. 1.

FIGS. 5 to 7 show examples of the operation of the surgical system 100. In FIGS. 5 and 6, the arm 3B and elements related to the arm 3B are depicted, and the other elements are omitted for the sake of convenience. In FIG. 7, the arm 3A and elements related to the arm 3A are depicted, and the other elements are omitted for the sake of convenience.

Referring to FIG. 1, in surgery using the patient-side system 1 configured as described above, a surgery assistant (or the operator S themselves) first moves the patient-side system 1 close to the surgical bed 111 by using the cart 70. During this movement, the positioner 7, arm base 5, and arms 3 are in given retracted positions (not shown) defined with respect to the cart 70.

Sleeves (cannula sleeves) 112 are retained on the body surface of the patient P lying on the surgical bed 111. For example, the sleeves 112 are arranged in a straight line in the lateral direction. The sleeves 112 are arranged in a single row in the direction orthogonal to the plane of FIG. 1. The sleeves 112 are not limited to being arranged in this manner.

The positioner 7 is controlled to position the arm base body 50 such that the arm base body 50 is located above the patient P and that the rotation axes R1 of the first joints J31 of the arms 3 mounted on the arm mounts 52 are oriented substantially in a horizontal direction. The angle between the rotation axis R1 of each first joint J31 and the horizontal plane is, for example, in the range of −30 degrees to +30 degrees. Additionally, the positioner 7 is controlled to position the arm base body 50 such that the second direction D2, in which the arm mounts 52 are oriented, is substantially parallel to the direction in which the sleeves 112 are arranged.

The surgery assistant sets remote centers RC (center points) in the controller 600. The remote centers RC are associated with the arms 3 in one-to-one correspondence. In the setting of each remote center RC, the surgery assistant attaches a surgical tool 40 for teaching to the holder 36 and, for example, moves the surgical tool 40 for teaching such that the distal end of the surgical tool 40 is located at the center of the hole of the sleeve 112. The surgery assistant then inputs to the operation interface 604 an instruction to set the remote center RC. In response to this instruction, the controller 600 performs forward transformation based on the posture of the arm 3, the positional relationship of the distal end of the shaft 43 of the surgical tool 40 for teaching relative to the tool base 45 of the surgical tool 40, the position and posture of the base 80, and information on parameters related to the arm links, thereby calculating the location of the remote center RC.

In the first direction D1, the arms 3 and the sleeves 112 are associated in one-to-one correspondence such that the remote centers RC associated respectively with the arms 3 are arranged in the order in which the arms 3 are arranged. That is, the rightmost sleeve 112 in the first direction D1 is associated with the rightmost arm 3A in the first direction D1. Upon calculation of the remote center RC for this sleeve 112, the arm 3A and the rightmost remote center RC in the first direction D1 are associated with each other. The same applies to the arms 3B, 3C, and 3D.

The surgery assistant or operator S replaces the surgical tool 40 for teaching by the endoscope assembly or instrument 42. Through the preliminary procedures as described above, the positioner 7, arm base 5, and arms 3 are positioned to establish a given initial positional relationship between the sleeves 112 retained on the body surface of the patient P that is the surgical site 110 and the surgical tools 40 attached to the arms 3.

In each arm 3 which is in the initial posture, the base 80 extends substantially in a horizontal direction. The second and third links 82 and 83 connected to the bent first link 81 extend obliquely downward. More specifically, the second and third links 82 and 83 extend downward in the direction (second direction D2) in which the rotation axis R1 of the first joint J31 extends from the proximal end to the distal end of the base 80 (direction towards the feet of the patient P in FIG. 6). The fourth link 84 is turned in the opposite direction at the elbow 31, and the fourth, fifth, and sixth links 84, 85, and 86 extend obliquely downward. More specifically, the fourth, fifth, and sixth links 84, 85, and 86 extend downward in the direction in which the rotation axis R1 of the first joint J31 extends from the distal end to the proximal end of the base 80 (direction towards the head of the patient P in FIG. 6). The initial posture of the arm 3 may be determined so as to meet additional constraints described later.

In the present embodiment, the controller 600 disables operation inputs received through the console 2 while the patient-side system 1 (the positioner 7, arm base 5, and arms 3) is moved from the retracted position to the preparatory position. Once the patient-side system 1 is placed in the preparatory position, the controller 600 enables operation inputs received through the console 2. During surgery subsequent to the placement of the patient-side system 1 in the preparatory position, the controller 600 basically keeps the positioner 7 and arm base 5 at rest, and in this state the arm controller 601 generates an operation command based on an input provided by the operator S operating the console 2. Thus, in response to the operation input received from the console 2, the arm controller 601 performs motion control to move the arm 3 of interest such that the position and posture of the surgical tool 40 are changed as desired. In the control of the arm 3, the arm controller 601 constrains the posture of the surgical tool 40 such that the surgical tool 40 inserted into the sleeve 112 passes through the remote center RC. This can restrict the sleeve 112 from moving in the in-plane direction of the body surface of the patient P.

Moving the surgical tool 40 to a target position and placing the surgical tool 40 in a target posture at the target position during surgery are accomplished through motions including joint motions involving the nine axes of the joints J31 to J39. Since each arm 3 has more than seven degrees of freedom and redundancy, the posture of the arm 3 is not uniquely determined for a given target position and target posture of the shaft 43 of the surgical tool 40. In particular, rotation of the shaft 43 in a circumferential direction about the central axis C of the shaft 43 can be effected not only by rotating the ninth joint J39 whose rotation axis coincides with the central axis C but also by rotating the distal end of the arm body 30 in the circumferential direction about the central axis C. Thus, the controller 600 combines a motion of the arm body 30 and a motion of the ninth joint J39 to rotate the shaft 43 in the circumferential direction about the central axis C. Additionally, when effecting the rotation of the shaft 43 in the circumferential direction about the central axis C, the controller 600 moves the arm body 30 and the ninth joint J39 in such a manner as to meet the additional constraints described below.

In setting of the additional constraints, first, the arm controller 601 sets a reference point RD for each arm 3 as shown in FIG. 5. Referring to FIG. 3, the reference point RDB of the arm 3B is located on a reference line RLB that is an extension of the rotation axis R1 of the first joint J31 of the arm 3B. The reference point RDA of the arm 3A is located on a reference line RLA (see also FIG. 7) which is offset to one side (+ direction) from the rotation axis R1 of the first joint J31 of the arm 3A in the first direction D1 (the direction normal to the rotation axis R1). In this operation example, the first direction D1 is a horizontal direction. Additionally, the first direction D1 is parallel to the longitudinal direction of the arm base 5. The reference point RDC of the arm 3C is located on a reference line RLC which is offset to the other side (− direction) from the rotation axis R1 of the first joint J31 of the arm 3C in the first direction D1. The reference point RDD of the arm 3D is located on a reference line RLD which is offset to the other side (− direction) from the rotation axis R1 of the first joint J31 of the arm 3D in the first direction D1. The offset distances of the reference lines RL of the arms 3 are set individually. This can reliably prevent each arm 3 from interfering with another component such as the adjacent arm 3 of the surgical system 100 or with the surrounding environment including the surgery assistant.

Referring to FIG. 6, the arm controller 601 subsequently determines whether a length L of a perpendicular line vh drawn from the reference point RD to the central axis C of the shaft 43 assuming the target posture at the target position is smaller than a predetermined minimum length Lmin. Upon determining that the length of the perpendicular line vh is smaller than the minimum length Lmin, the arm controller 601 moves the reference point RD on the reference line RL in a direction away from the central axis C of the shaft 43 such that the length of the perpendicular line vh becomes greater than the predetermined length Lmin. The arm controller 601 does not perform this process in case that the length of the perpendicular line vh is determined to be greater than the minimum length Lmin. The arm controller 601 need not make the above determination, and may choose the location of the reference point RD on the reference line RL based on a continuous function defining the relationship between the length L of the perpendicular line vh and the location of the reference point RD on the reference line RL.

Referring to FIG. 5, the arm controller 601 subsequently positions the joints J31 to J39 such that the reference plane RP passes through the reference point RD. As previously stated, the reference plane RP is a plane including the rotation axis R9 of the ninth joint J39 which extends in the long axis direction Dt and orthogonal to the rotation axis R7 of the seventh joint J37.

Thus, the postures of the translational motion unit 35 and tool base 45 are constrained such that the translational motion unit 35 and tool base 45 pivot about an axis line Rv connecting the reference point RD and the remote center RC. As such, when effecting rotation of the shaft 43 in the circumferential direction about the central axis C, the required proportion of rotation of the distal end of the arm body 30 in the circumferential direction about the central axis C can be reduced. Additionally, the proportion of rotation of the ninth joint J39 can be increased for rotation of the shaft 43. Thus, the translational motion unit 35 is located in a direction orthogonal to the seventh joint J37, and the arm controller 601 can place the arm 3 in a posture in which the translational motion unit 35 is located outside the seventh joint J37 with respect to the reference point RD. This can prevent the translational motion unit 35 and tool base 45 from assuming a posture in which the translational motion unit 35 and tool base 45 protrude laterally (first direction D1) from the arm body 30. As a result, interference of each arm 3 with another component such as the adjacent arm 3 of the surgical system 100 or with the surrounding environment can be prevented. Additionally, since the arm 3 can be placed in a posture in which the sixth link 86 of the arm body 30 is directed from the seventh joint J37 towards the center of the arm 3, the link length of the arm body 30 can be effectively utilized, and the movement range of the arm 3 can be extended. Furthermore, since the arms 3 are placed in such postures as to spread in a fan shape from the arm base body 50, interference between the adjacent arms can be reduced.

In a situation where, for example, the shaft 43 has pivoted upward about the remote center RC and moved towards the reference point RD as shown in FIG. 6, the radius of rotation in the movement of the distal end of the arm body 30 about the central axis C could be small during rotation of the shaft 43 about the central axis C. As a result, the motion response of the arm body 30 could be excessively high, and the translational motion unit 35 and tool base 45 could be subjected to intense vibrations or suffer reduced responsivity due to rapid motion of the arm body 30. However, upon determining that the length L of the perpendicular line vh is smaller than the minimum length Lmin, the arm controller 601 moves the reference point RD on the reference line RL such that the length of the perpendicular line vh becomes greater than the predetermined length Lmin. Thus, the radius of rotation in the movement of the distal end of the arm body 30 about the central axis C can be prevented from being small owing to the closeness of the shaft 43 to the reference point RD, and this can avoid excessively high motion response of the arm body 30. In the case where the arm controller 601 chooses the location of the reference point RD on the reference line RL based on a continuous function defining the relationship between the length L of the perpendicular line vh and the location of the reference point RD on the reference line RL, the occurrence of excessively high motion response can be avoided.

As described above, the arm controller 601 controls the arm 3 such that the shaft 43 of the surgical tool 40 assumes the target posture at the target position. Once a new target position and target posture are set, the arm controller 601 repeats the process starting from the determination of whether the length L of the perpendicular line vh is smaller than the predetermined minimum length Lmin.

Embodiment 2

Figure 8:
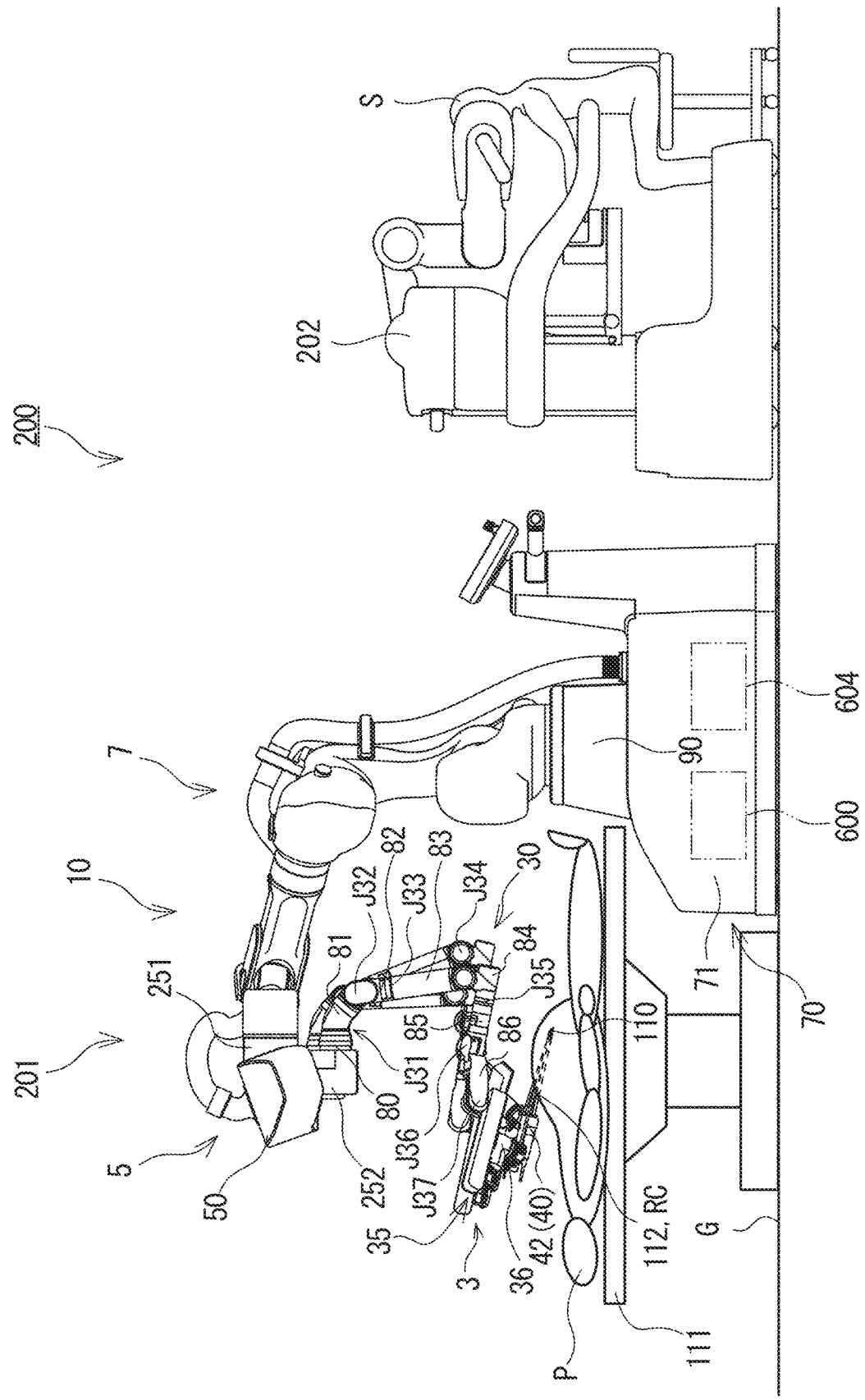
FIG. 8 is a front view showing an example of the configuration of a surgical system according to Embodiment 2.

FIG. 8 is a front view showing an example of the configuration of a surgical system 200 according to Embodiment 2.

An arm mount 252 of the surgical system 200 according to Embodiment 2 is disposed to face the same side as a positioner mount 251 in the second direction D2. In other respects, the configurations of a patient-side system 201 and console 202 of the surgical system 200 are the same as the configurations of the patient-side system 1 and console 2 of the surgical system 100 according to the previous embodiment. The configurations of the patient-side system 201 and console 202 will therefore not be described in detail.

Figure 9:
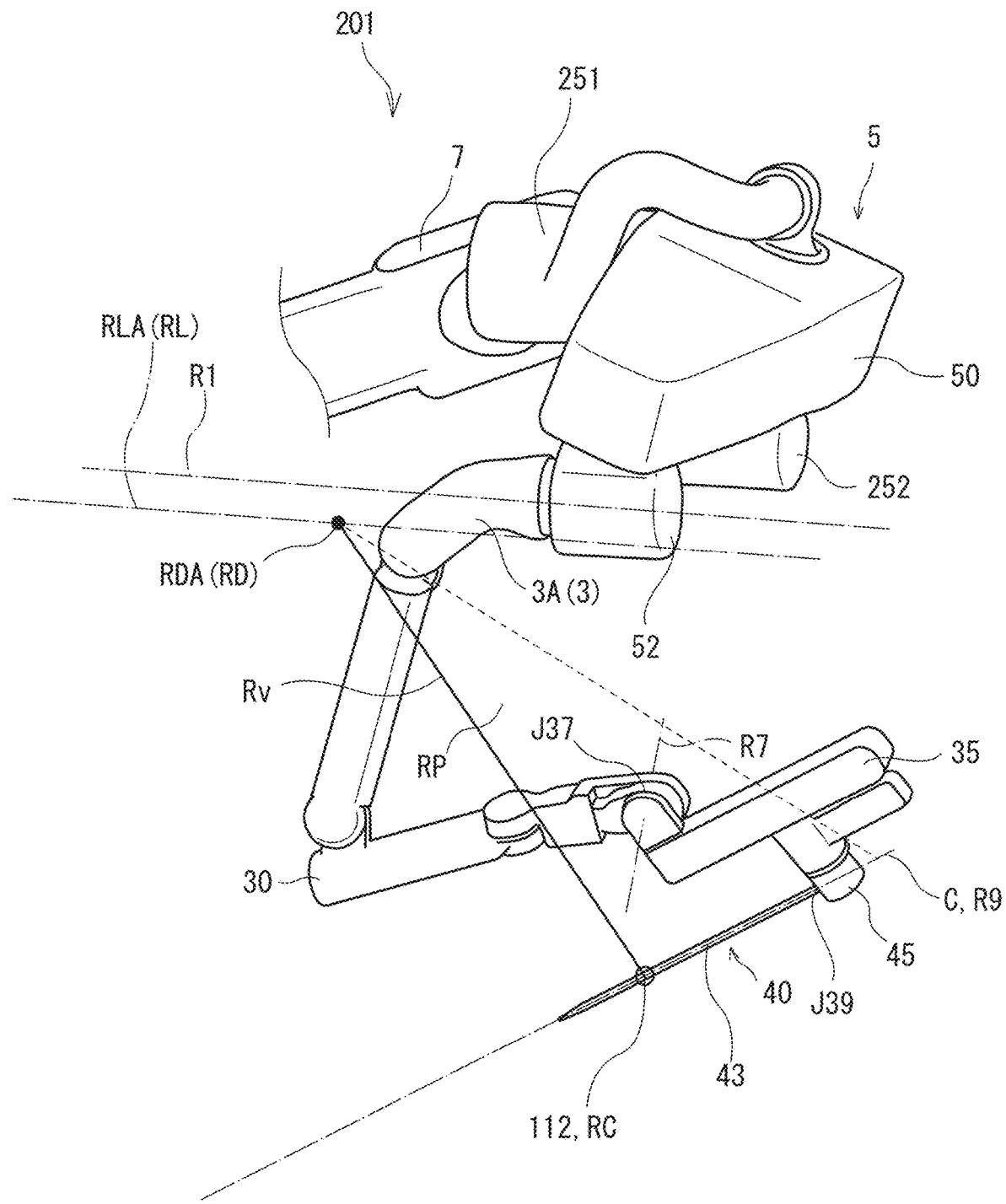
FIG. 9 shows an example of the operation of the surgical system of FIG. 8.

FIG. 9 shows an example of the operation of the surgical system 200. The example of the operation of the surgical system 200 is the same as that of the surgical system 100. In FIG. 9, the arm 3A and elements related to the arm 3A are depicted, and the other elements are omitted. Although the patient P is also omitted in FIG. 9, the posture of the patient P relative to the arm 3 is the same as in FIGS. 5 and 6.

From the foregoing description, numerous modifications and other embodiments of the present invention are obvious to those skilled in the art. Accordingly, the foregoing description is to be construed as illustrative only, and is provided for the purpose of teaching those skilled in the art the best mode for carrying out the present invention. The structural and/or functional details may be substantially modified without departing from the scope of the present invention.

The invention claimed is:

1. A surgical system comprising:
   a surgical tool including a shaft and a distal end roll joint having a rotation axis coinciding with a central axis of the shaft;
   a manipulator arm holding the surgical tool at a distal end thereof and having seven or more degrees of freedom, the manipulator arm including joints and actuators that drive the joints to effect positioning of the joints, the joints including a proximal end roll joint disposed at a proximal end of the manipulator arm and a pivotal joint disposed between the proximal end roll joint and the distal end roll joint, the pivotal joint having a rotation axis crossing a reference plane including the rotation axis of the distal end roll joint, the rotation axis of the pivotal joint being in a fixed orientation relative to the reference plane;
   a console that receives an operation input provided by an operator to the manipulator arm; and
   a controller that controls the actuators based on the operation input, wherein
   the controller is configured to: set a center point; set a reference point on a reference line that is offset from an extension of a rotation axis of the proximal end roll joint in a direction normal to the extension; and position the joints such that the shaft passes through the center point and that the reference plane passes through the reference point.

2. The surgical system according to claim 1, wherein the controller is configured to, when a length of a perpendicular line drawn from the reference point to the central axis of the shaft is smaller than a predetermined length, move the reference point on the reference line such that the length of the perpendicular line becomes greater than the predetermined length.

3. The surgical system according to claim 1, further comprising a plurality of the manipulator arms, wherein offset distances of the reference lines of the manipulator arms are set individually.

4. The surgical system according to claim 1, wherein the joints include a prismatic joint disposed between the pivotal joint and the distal end roll joint.

5. The surgical system according to claim 1, wherein the reference line is offset from the extension of the rotation axis of the proximal end roll joint in a horizontal direction normal to the extension.

6. The surgical system according to claim 1, further comprising an arm base having an elongated shape and holding the proximal ends of a plurality of the manipulator arms, wherein
the reference line is offset from the extension of the rotation axis of the proximal end roll joint in a direction normal to the extension and parallel to a longitudinal direction of the arm base.

7. A method of controlling a surgical manipulator arm, the surgical manipulator arm including: a surgical tool including a shaft and a distal end roll joint having a rotation axis coinciding with a central axis of the shaft; and a manipulator arm holding the surgical tool at a distal end thereof and having seven or more degrees of freedom, the manipulator arm including joints and actuators that drive the joints to effect positioning of the joints, the joints including a proximal end roll joint disposed at a proximal end of the manipulator arm and a pivotal joint disposed between the proximal end roll joint and the distal end roll joint, the pivotal joint having a rotation axis crossing a reference plane including the rotation axis of the distal end roll joint, the rotation axis of the pivotal joint being in a fixed orientation relative to the reference plane, the method comprising:
setting a center point;
setting a reference point on a reference line that is offset from an extension of a rotation axis of the proximal end roll joint in a direction normal to the extension;
based on an operation input received from an operator, setting a target position and posture in which the shaft passes through the center point; and
positioning the joints such that the shaft assumes the target posture at the target position and that the reference plane passes through the reference point.

8. The surgical system according to claim 1, wherein
the rotation axis of the pivotal joint is orthogonal to the reference plane, and
the reference point is a point at which the reference plane and the reference line cross each other.

9. The surgical system according to claim 2, wherein the controller is configured to move the reference point on the reference line away from the central axis of the shaft.

10. The surgical system according to claim 1, wherein the center point is located such that the surgical tool passes through the center point when the controller moves the manipulator arm to change a position and posture of the surgical tool.

11. The surgical system according to claim 10, further comprising an operation interface, wherein
the center point is set based on an input provided to the operation interface.

12. The method according to claim 7, wherein
the rotation axis of the pivotal joint is orthogonal to the reference plane, and
the reference point is a point at which the reference plane and the reference line cross each other.

13. The method according to claim 7, wherein when a length of a perpendicular line drawn from the reference point to the central axis of the shaft is smaller than a predetermined length, the reference point is moved on the reference line such that the length of the perpendicular line becomes greater than the predetermined length.

14. The method according to claim 13, wherein the reference point is moved on the reference line away from the central axis of the shaft.

15. The method according to claim 7, wherein
the surgical manipulator arm further includes a plurality of the manipulator arms, and
offset distances of the reference lines of the manipulator arms are set individually.

16. The method according to claim 7, wherein the joints include a prismatic joint disposed between the pivotal joint and the distal end roll joint.

17. The method according to claim 7, wherein the reference line is offset from the extension of the rotation axis of the proximal end roll joint in a horizontal direction normal to the extension.

18. The method according to claim 7, wherein
the surgical manipulator arm further includes an arm base having an elongated shape and holding the base ends of the manipulator arms, and
the reference line is offset from the extension of the rotation axis of the proximal end roll joint in a direction normal to the extension and parallel to a longitudinal direction of the arm base.

19. The method according to claim 7, wherein the center point is located such that the surgical tool passes through the center point when the manipulator arm is moved to change a position and posture of the surgical tool.

20. The method according to claim 19, wherein
the surgical manipulator arm further includes an operation interface, and
the center point is set based on an input provided to the operation interface.

21. A surgical system comprising:
a surgical tool including a shaft and a distal end roll joint having a rotation axis coinciding with a central axis of the shaft;
a manipulator arm holding the surgical tool at a distal end thereof and having seven or more degrees of freedom, the manipulator arm including joints and actuators that drive the joints to effect positioning of the joints, the joints including a proximal end roll joint disposed at a proximal end of the manipulator arm and a pivotal joint disposed between the proximal end roll joint and the distal end roll joint, the pivotal joint having a rotation axis crossing a reference plane including the rotation axis of the distal end roll joint, the rotation axis of the pivotal joint being in a fixed orientation relative to the reference plane;
a console that receives an operation input provided by an operator to the manipulator arm; and
a controller that controls the actuators based on the operation input, wherein
the controller is configured to: set a center point; set a reference point on a reference line that is an extension of a rotation axis of the proximal end roll joint or that is offset from the extension in a direction normal to the extension; and position the joints such that the shaft passes through the center point and that the reference plane passes through the reference point, and
the controller is configured to, when a length of a perpendicular line drawn from the reference point to the central axis of the shaft is smaller than a predetermined length, move the reference point on the reference line such that the length of the perpendicular line becomes greater than the predetermined length.

* * * * *